(12) United States Patent
Chen et al.

(10) Patent No.: US 10,662,145 B2
(45) Date of Patent: May 26, 2020

(54) METHOD OF SYNTHESIZING DICLOFENAC SODIUM

(71) Applicant: FUDAN UNIVERSITY, Shanghai (CN)

(72) Inventors: Fener Chen, Shanghai (CN); Lingdong Wang, Shanghai (CN); Ge Meng, Shanghai (CN); Zedu Huang, Shanghai (CN); Dang Cheng, Shanghai (CN); Haihui Peng, Shanghai (CN); Guanfeng Liang, Shanghai (CN)

(73) Assignee: FUDAN UNIVERSITY, Shanghai (CN)

( * ) Notice: Subject to any disclaimer, the term of this patent is extended or adjusted under 35 U.S.C. 154(b) by 0 days.

(21) Appl. No.: 16/288,031

(22) Filed: Feb. 27, 2019

(65) Prior Publication Data
US 2020/0055811 A1    Feb. 20, 2020

(30) Foreign Application Priority Data

Aug. 17, 2018  (CN) .......................... 2018 1 0943569

(51) Int. Cl.
*C07C 227/18* (2006.01)
*C07C 201/08* (2006.01)
*C07C 227/16* (2006.01)
*C07C 227/06* (2006.01)

(52) U.S. Cl.
CPC .......... *C07C 227/18* (2013.01); *C07C 201/08* (2013.01); *C07C 227/06* (2013.01); *C07C 227/16* (2013.01); *C07C 2601/16* (2017.05)

(58) Field of Classification Search
None
See application file for complete search history.

(56) References Cited

U.S. PATENT DOCUMENTS 4,978,773 A * 12/1990 Grafe .................... C07C 227/18
548/486

* cited by examiner

*Primary Examiner* — Sudhakar Katakam
*Assistant Examiner* — Jennifer C Sawyer
(74) *Attorney, Agent, or Firm* — Wayne & Ken, LLC; Tony Hom

(57) ABSTRACT

The invention relates to the chemical synthesis of pharmaceutical API, and specifically to a method of synthesizing diclofenac sodium, which is a kind of nonsteroidal anti-inflammatory drug for relieving pain. The method includes: nitrating phenylacetate to prepare o-nitrophenylacetate (2); hydrogenating o-nitrophenylacetate (2) to prepare o-aminophenylacetate (3); amidating an amino group of o-aminophenylacetate (3) to obtain 2-(2-benzoylaminophenyl) acetate (4); 2-(2-benzoylaminophenyl) acetate (4) reacting with thionyl chloride to prepare a chloroimine intermediate, and then condensing the intermediate of chloroimine with 2,6-dichlorophenol using an inorganic base to prepare (E)-methyl-2-(2-((2,6-dichlorophenoxy)(phenyl)methyl-eneamino) phenyl ester (5); subjecting (E)-methyl-2-(2-((2,6-dichlorophenoxy)(phenyl)methyleneamino) phenyl ester (5) to Chapman rearrangement to afford methyl 2-(2-(N-(2,6-dichlorophenyl)benzoylamino)phenyl) ester (6); and hydrolyzing methyl 2-(2-(N-(2,6-dichlorophenyl)benzoylamino)phenyl) ester (6) to provide the target compound as of diclofenac sodium API. The overall yield is up to 67% based on methyl phenylacetate.

10 Claims, 4 Drawing Sheets

METHOD OF SYNTHESIZING DICLOFENAC SODIUM

CROSS-REFERENCE TO RELATED APPLICATIONS

This application claims priority from Chinese Patent Application No. 201810943569.X, filed on Aug. 17, 2018, which is hereby incorporated by reference in their entireties.

TECHNICAL FIELD

The present disclosure relates to the chemical synthesis of an active pharmaceutical ingredient (API), and specifically relates to a method of synthesizing diclofenac sodium (Voltaren).

BACKGROUND OF THE INVENTION

Diclofenac sodium is a nonsteroidal anti-inflammatory drug (NSAID) used to treat pain, which was available as a potent aryl-acetic acid drug in 1974. Diclofenac sodium is used clinically for relieving fever or pain. It is widely used for treating chronic rheumatoid arthritis, spinal deformity, neuralgia, flu-like syndrome, lupus erythematosus, and post-operative pain and inflammation, etc. Diclofenac sodium has been favored by doctors and patients because of its good efficacy, fast absorption by oral administration, fast action and excretion, little side effects during long-term use, and small differences between individuals. The chemical structural formula of diclofenac sodium is shown as (1):

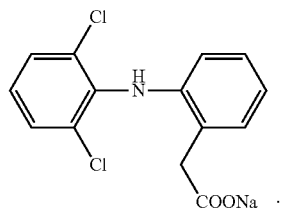

1

GB Patent No. 1132128 and U.S. Pat. No. 3,558,690 disclose a method for producing diclofenac sodium (1), where o-(bromo)benzoic acid was used as a the starting material to prepare the key intermediate 2,6-dichlorodiphenylamine by Ullmann condensation and decarboxylation. 2,6-Dichlorodiphenylamine was then subjected to acylation, cyclization and ring-opening hydrolysis/salification to obtain diclofenac sodium (1). This method was the earliest synthetic route for the industrial production of diclofenac sodium in China, which involved the commercially available raw materials. However, such process was longtime consuming with the low total yield and the serious environmental pollution. NL Patent No. 6604752 and JP Patent No. 23418 disclosed a method of synthesizing 2,6-dichlorodiphenylamine with bromobenzene and 2,6-dichloroaniline by Ullmann condensation with a yield of nearly 50%. This method has been widely used in the past, but its industrial application was very limited because a small amount of by-products such as N-phenyl-2-chloro-6-bromoaniline produced during synthesis was difficult to separate. Besides, the traces of aromatic bromide may cause the side effects such as stomach ulcers. EP Patent No. 0380712 and WO Patent No. 022522 discloses a method of producing diclofenac sodium (1) in three steps in a one-pot including acylation, etherification and Chapman rearrangement, where aniline was used as a starting material. Fen'er Chen et al. (Chinese Journal of Pharmaceuticals, 1998, 29, 339) make improvements to such method, but leading to the serious pollution caused by wastes, high labor safety requirements and greatly increased costs. Fen'er Chen et al. (Chinese Patent Publication No. CN 1580039A) discloses a method for synthesizing diclofenac sodium (1) using cyclohexanone as a starting material though a series of chlorination, carboxylation, hydrogenation, condensation, and aromatization/salification. Although this method involved a high yield, its industrial application was limited due to the long process and highly toxic organophosphorus reagent. U.S. Pat. No. 4,978,773 and Bingchang Qin et al. (Applied Chemical Industry, 2008, 3, 275) disclose a method of producing diclofenac sodium in which 2,6-dichlorodiphenylamine and chloroacetyl chloride are used as primary raw materials, followed by acylation, intramolecular Friedel-Craft alkylation and alkaline hydrolysis ring-opening reaction. But in this method, the reaction process was longtime consuming with the relatively low overall yield.

Therefore, there is an urgent need to develop a method for synthesizing diclofenac sodium with the high yield and low cost to overcome the defects in the above methods.

SUMMARY OF THE INVENTION

The object of the present invention is to provide a method of synthesizing diclofenac sodium (1) using phenylacetate as the raw material, resulting in high yield, low cost and energy consumption, and less pollution to overcome the defects in the prior art.

The present invention provides a method of synthesizing diclofenac sodium (1), as shown in the following reaction scheme:

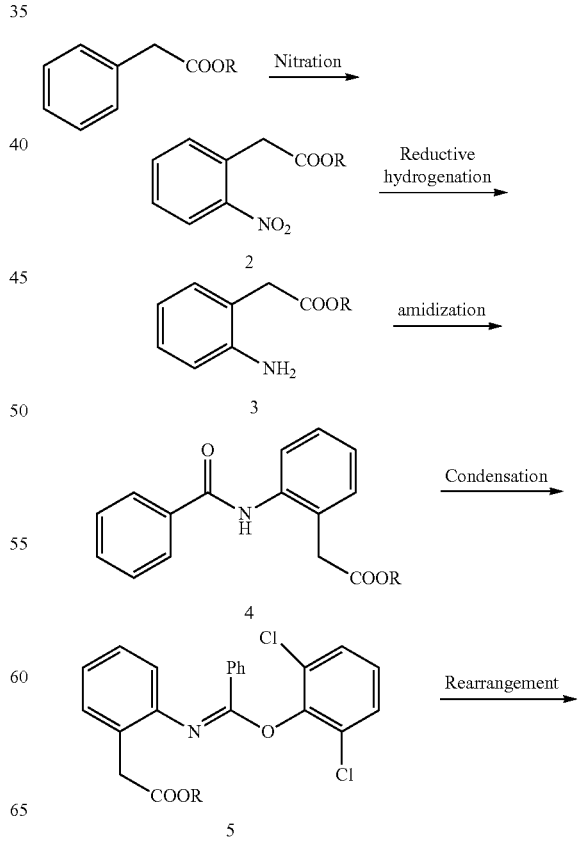

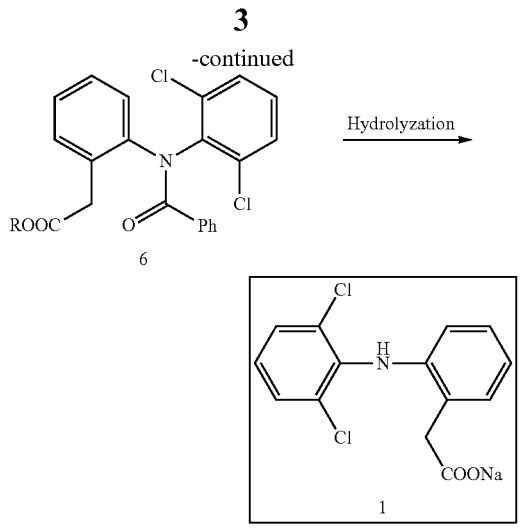

wherein, R is a $C_1$-$C_8$ alkyl group or cycloalkyl group, a monosubstituted or polysubstituted aryl or alkyl group.

The method of the invention comprises the following steps:

step (1) ortho-nitrating phenylacetate in a concentration of dichloromethane solution containing a nitration agent (such as fuming nitric acid, concentrated nitric acid) to obtain o-nitrophenylacetate (2);

step (2) hydrogenating o-nitrophenylacetate (2) in the presence of a palladium catalyst to obtain o-aminophenylacetate (3);

step (3) amidating an amino group of o-aminophenylacetate (3) to obtain 2-(2-benzoylaminophenyl) acetate (4);

step (4) 2-(2-benzoylaminophenyl) acetate (4) reacting with thionyl chloride to obtain a chloroimine intermediate, and then condensing the chloroimine intermediate with 2,6-dichlorophenol using an inorganic base to obtain (E)-methyl-2-(2-((2,6-dichlorophenoxy)(phenyl)methyleneamino)phenyl) ester (5);

step (5) subjecting (E)-methyl-2-(2-((2,6-dichlorophenoxy)(phenyl)methylene amino)phenyl)ester (5) to Chapman rearrangement to obtain methyl 2-(2-(N-(2,6-dichlorophenyl)benzoylamino)phenyl)ester (6); and step (6) hydrolyzing methyl 2-(2-(N-(2,6-dichlorophenyl)benzoylamino)phenyl) ester (6) with an inorganic base to obtain a target product diclofenac sodium (1).

The method of the invention reaches a total yield of about 67%, based on benzoate. The analytical data of the resulting product meets the quality standards as specified in USP, BP, Japanese Pharmacy and Chinese Pharmacopoeia.

In step (1), the nitration agent is selected from nitric acid, fuming nitric acid, a mixture of nitric acid and sulfuric acid, or a mixture of nitric acid and acetic acid; an organic solvent is absent or selected from dichloromethane, tetrahydrofuran, dioxane or a mixture thereof; and a reaction temperature is −10~25° C.

In step (1), the nitration agent is preferably fuming nitric acid, or a mixture of nitric acid and sulfuric acid; an organic solvent is absent or is dichloromethane; and a reaction temperature is 0~25° C.

In step (2), the palladium catalyst is selected from the group consisting of Pd/C, D61-Pd, D72-Pd, D152-Pd, D261-Pd and D296-Pd; a hydrogenation pressure is from atmospheric pressure to 1.0 Mpa; an organic solvent is an alcohol of low molecular weight or an ester of low molecular weight; the organic solvent may be a single solvent, or a mixed solvent; and a reaction temperature is 0~50° C.

Preferably, the palladium catalyst is Pd/C; the hydrogenation pressure is atmospheric pressure; the organic solvent is selected from the group consisting of methanol, ethanol and ethyl acetate; and the reaction temperature is 5~25° C.

In step (3), an amidating agent is benzoyl chloride; an acid catcher is selected from the group consisting of triethylamine, potassium carbonate and sodium carbonate; and a reaction temperature is 0~30° C.

In step (4), the inorganic base is selected from the group consisting of sodium carbonate, potassium carbonate, sodium hydrogencarbonate and sodium hydride; an organic solvent is selected from the group consisting of dichloromethane, dichloroethane, tetrahydrofuran, toluene and xylene; and a reaction temperature is 60~130° C.

Preferably, the inorganic base is selected from the group consisting of sodium carbonate and potassium carbonate; and the organic solvent is toluene.

In step (5), an organic solvent is absent or selected from the group consisting of toluene, xylene and diphenyl ether; and a reaction temperature is 110~300° C.

In step (6), the inorganic base is sodium hydroxide; an organic solvent is selected from the group consisting of toluene and methanol; and a reaction temperature is 50~150° C.

In the method of the present invention, the raw materials are cheap and readily available. The usage of the various inorganic bases and the high-efficiency inorganic catalysts results in the simple work-ups, less pollution and high solvent recovery. Therefore, this method effectively solves the various problems arising from the traditional synthetic routes, which is suitable for the industrial production.

DETAILED DESCRIPTION OF EMBODIMENTS

Figure 1:
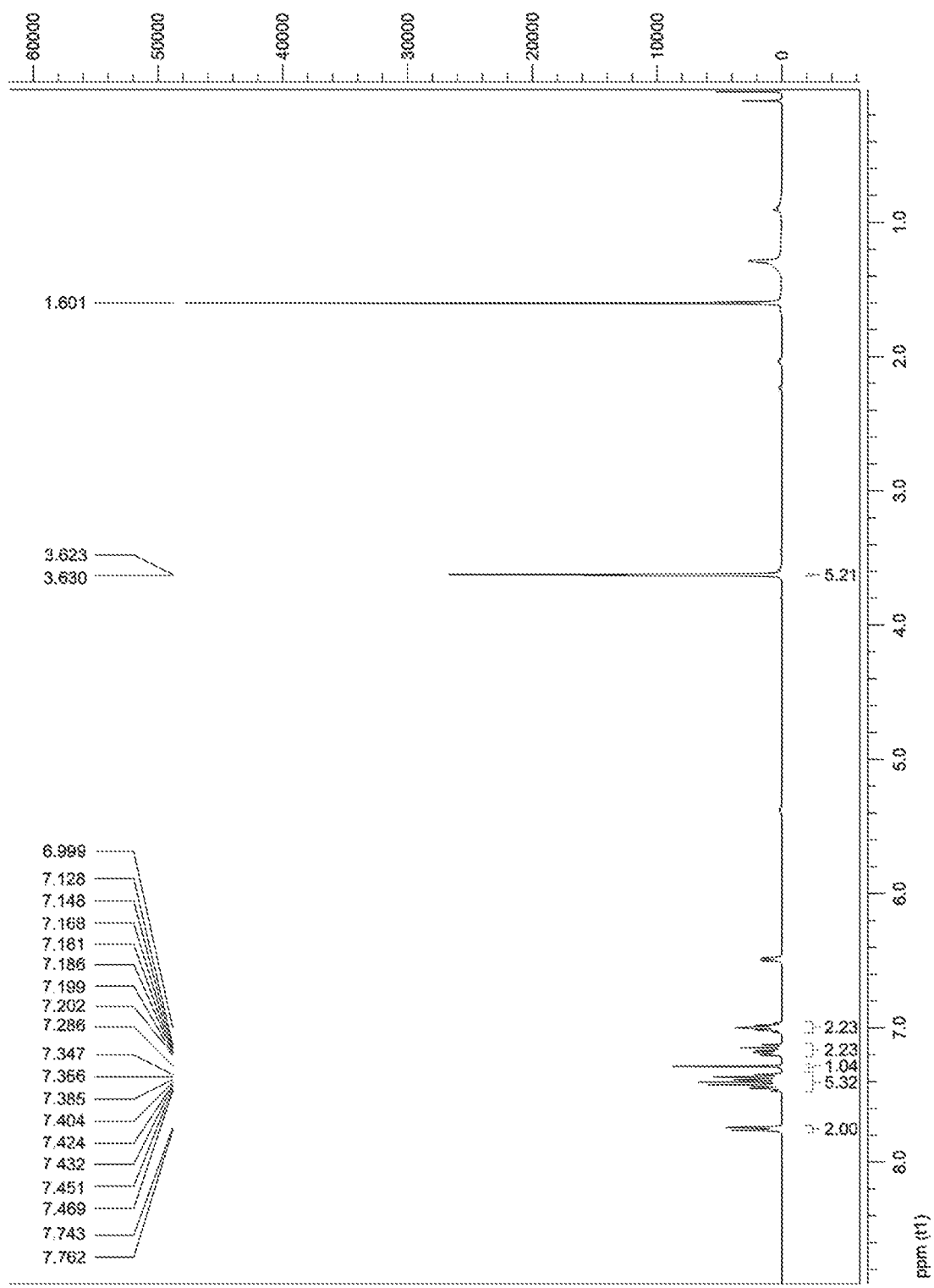
FIG. 1 shows $^1$H NMR of (E)-methyl 2-(2-((2,6-dichlorophenoxy) phenyl methyleneamino)phenyl ester (5).
Figure 2:
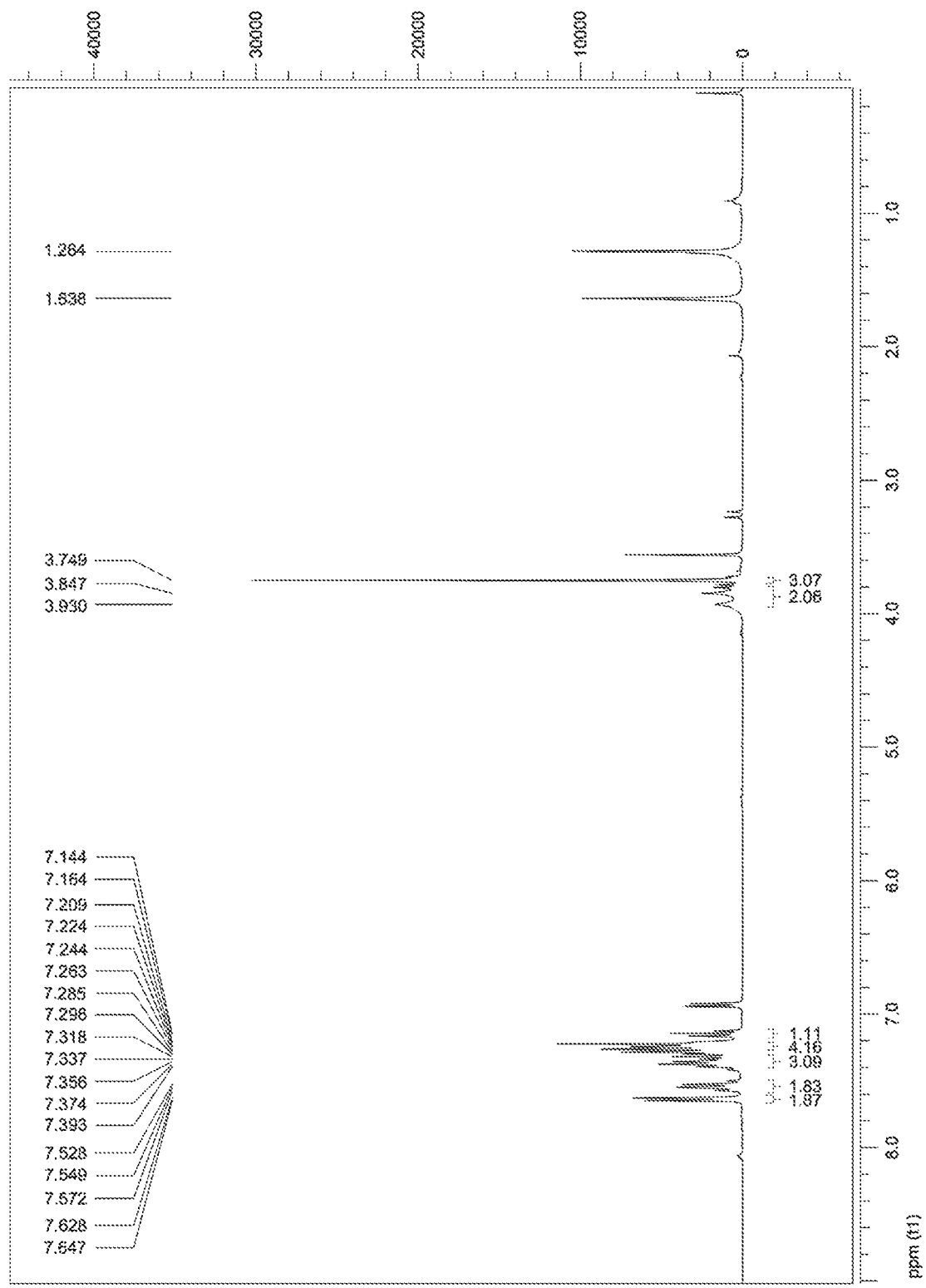
FIG. 2 shows $^1$H NMR of methyl 2-(2-(N-(2,6-dichlorophenyl) benzoylamino)phenyl) ester (6).
Figure 3:
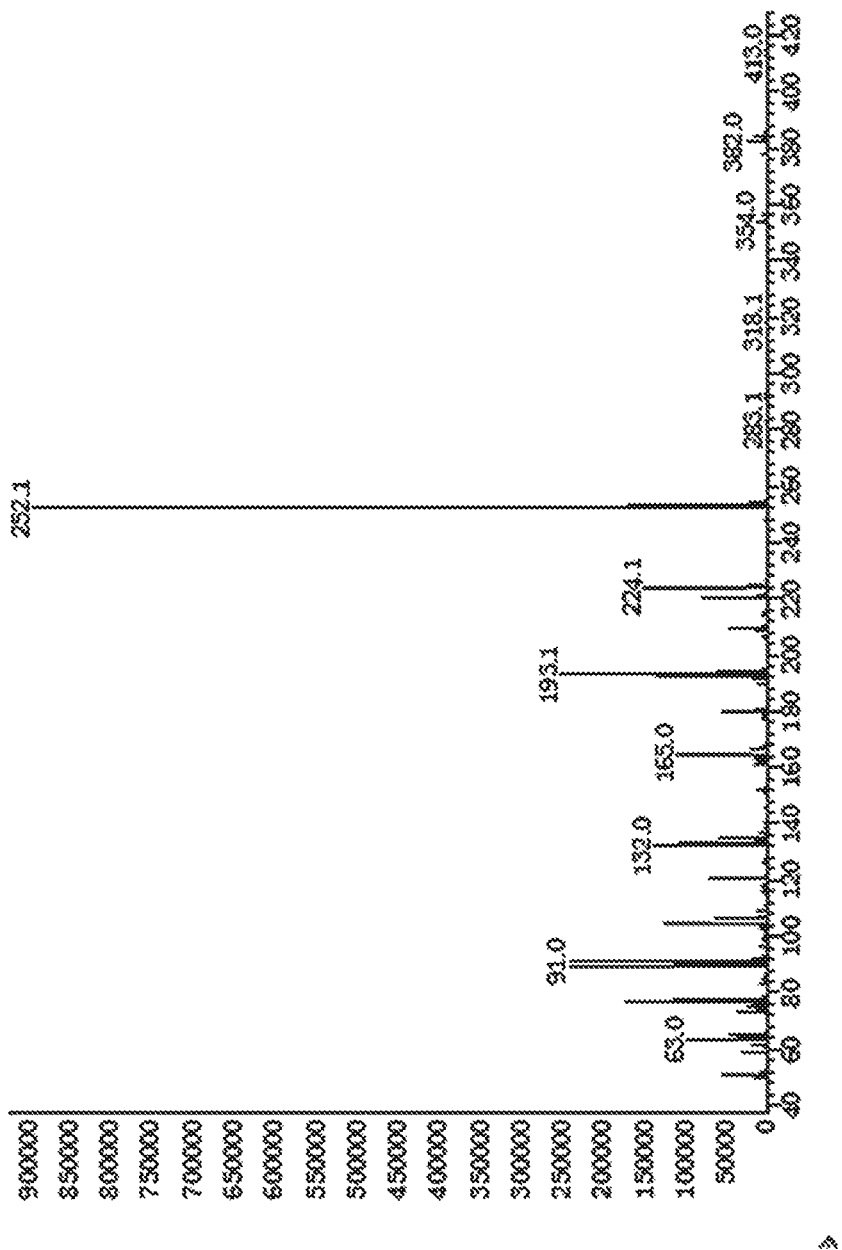
FIG. 3 shows a mass spectrum of (E)-methyl-2-(2-((2,6-dichlorophenoxy) phenyl methyleneamino)phenyl) ester (5).
Figure 4:
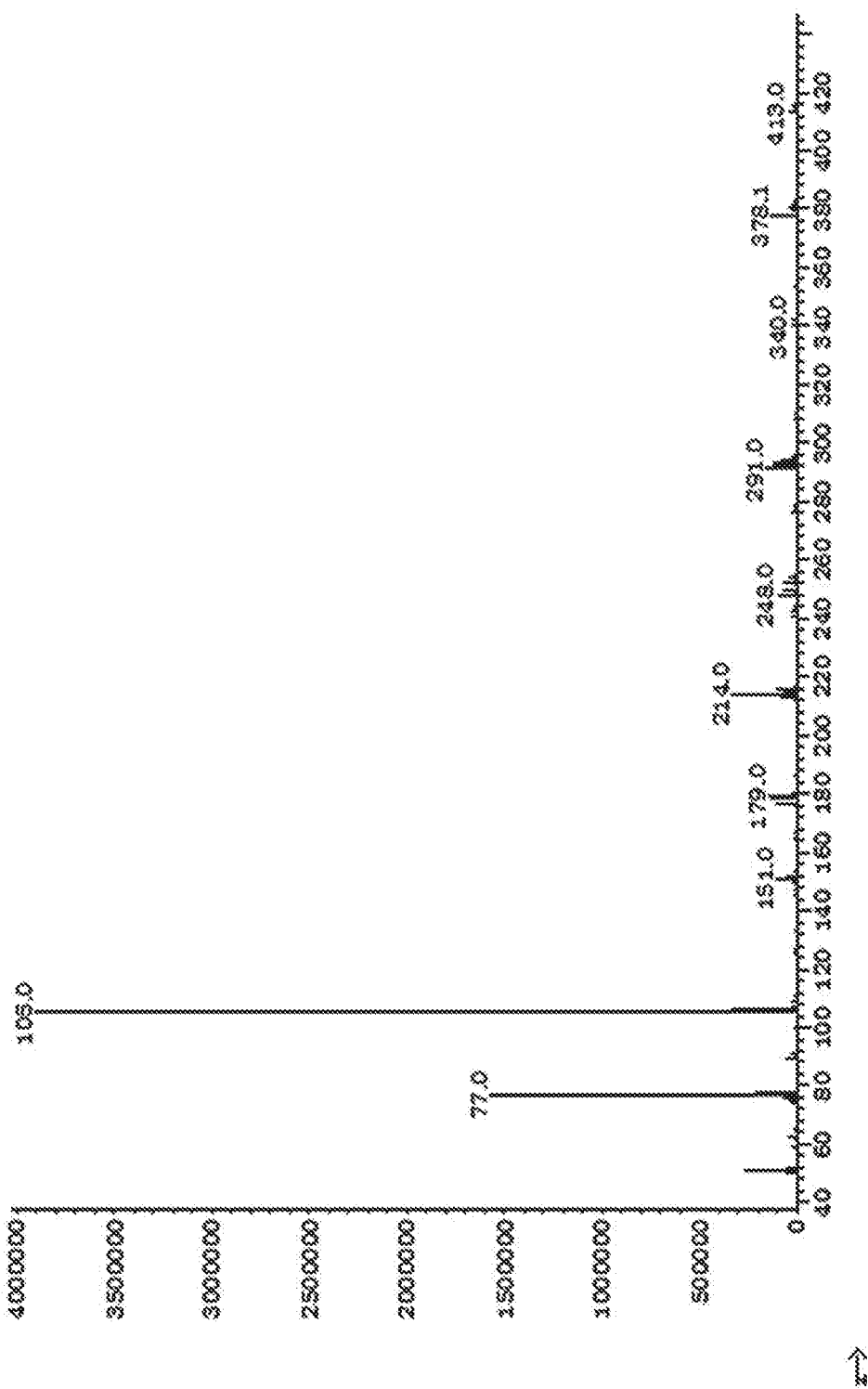
FIG. 4 shows a mass spectrum of methyl 2-(2-(N-(2,6-dichlorophenyl) benzoylamino)phenyl) ester (6).

The following embodiments are intended to further illustrate the features of the present invention, but are not intended to limit the scope of the application.

Preparation of o-nitrophenylacetate (2)

Example 1

Methyl phenylacetate (50 g, 0.33 mol) and dichloromethane (66 mL) were placed in a dry flask with vigorous stirring at 0° C. Fuming nitric acid (104 g, 1.65 mol) and dichloromethane (66 mL) solution were slowly added dropwisely. Then, the reaction mixture was warmed to room temperature and continuously stirred for 1 hour. The reaction was monitored by TLC. After the reaction was completed, the reaction solution was washed to neutral with water to form two layer including an organic phase, which was washed with sodium sulfate (10%), concentrated, and distilled under the reduced pressure to obtain a pale yellow liquid as the intermediate 2 (41.4 g, 64% yield), b.p., 112~116° C.

Example 2

Methyl phenylacetate (45 g, 0.3 mol) and dichloromethane (1500 mL) were placed in a dry flask and stirred vigorously at 0° C. Fuming nitric acid (189 g, 3 mol) and dichloromethane (462 mL) solution were slowly added dropwisely. Then, the reaction mixture was warmed to room temperature and continuously stirred for 24 hours. The reaction was monitored by TLC. After the reaction was completed, the reaction solution was washed to neutral with water to form two layer including an organic phase, which was washed with sodium sulfate (10%), concentrated, and distilled under the reduced pressure to obtain a pale yellow liquid as the intermediate 2 (49.2 g, 84% yield), b.p., 113~115° C.

Preparation of o-aminophenylacetate (3)

Example 1

The intermediate 2 (97.6 g, 0.5 mol), Pd/C (0.98 g) and toluene (200 mL) were placed in a flask, which was hydrogenated by injecting hydrogen overnight under the atmospheric pressure at 5° C. Then, the reaction mixture was filtered to give a residue, which was washed with a small amount of toluene. The filtrate and the washing liquid were combined. Toluene was recovered to give a residue, which was dried under vacuum to afford a pale yellow liquid as the intermediate 3 (80.9 g, 98% yield), b.p., 255~257° C.

Example 2

The intermediate 2 (97.6 g, 0.5 mol), D61-Pd (1.2 g) and methanol (200 mL) were placed in a flask, and hydrogenated by inletting hydrogen overnight under the atmospheric pressure at room temperature. Then, the reaction product was filtered and the residue was washed with a small amount of methanol. The filtrate and the washing liquid were combined. Methanol was recovered to give a residue, which was dried under vacuum to provide a pale yellow liquid as the intermediate 3 (80.1 g, 97% yield), b.p., 255~257° C.

Preparation of 2(2-benzoylaminophenyl) acetate (4)

Example 1

The intermediate 3 (66 g, 0.4 mol), triethylamine (40.5 g, 0.4 mol) and toluene (200 mL) were placed in a flask. Then benzoyl chloride (56.2 g, 0.4 mol) was dropwise added slowly in 1 hour under stirring at 0° C. After the reaction mixture was stirred for 1 hour, the reaction solution was filtered to obtain a filter cake and a filtrate. The filter cake and the filtrate were washed with water followed by concentration under vacuum to give the solids. The solids were combined to give a white solid as the intermediate 4 (105.6 g, 98% yield), m.p., 103~105° C.

Example 2

The intermediate 3 (66 g, 0.4 mol), sodium bicarbonate (33.6 g, 0.4 mol) and toluene (200 mL) were placed in a flask. Then benzoyl chloride (56.2 g, 0.4 mol) was dropwise added slowly in 1 hour under stirring at 0° C. After the reaction was stirred for 1 hour, the reaction solution was filtered to obtain a filter cake and a filtrate. The filter cake and the filtrate were washed with water followed by concentration under vacuum to give solids. The solids were combined to afford a white solid as the intermediate 4 (102.7 g, 95.3% yield), m.p., 102~104° C.

Preparation of (E)-methyl-2-(2-((2,6-dichlorophenoxy)(phenyl) methyleneamino) phenyl) ester (5)

Example 1

The intermediate 4 (94.3 g, 0.35 mol) and thionyl chloride (200 mL) were placed in a flask and refluxed for 3 hours. Thionyl chloride was recovered under reduced pressure to give a pale yellow oil for the further usage. 2,6-Dichlorophenol (57.1 g, 0.35 mol), sodium carbonate (37.1 g, 0.35 mol) and toluene (200 mL) were placed in a flask, and the above pale yellow oil was dropwise added slowly into an ice bath. Then the reaction mixture was heated to reflux for 3 hours. The reaction solution was filtered to remove insoluble materials. The filtrate was washed with water, concentrated and dried under vacuum to provide an orange solid as the intermediate 5 (139.2 g, 96% yield), m.p., 135~137° C. $^1$H NMR (400 MHz, CDCl$_3$) δ: 7.75 (d, J=7.6 Hz, 2H), 7.47-7.35 (m, 5H), 7.29 (s, 1H), 7.20-7.13 (m, 2H), 7.03-7.70 (m, 2H), 3.63 (s, 2H), 3.62 (s, 3H).

Example 2

The intermediate 4 (94.3 g, 0.35 mol) and thionyl chloride (200 mL) were placed in a flask and refluxed for 3 hours. Thionyl chloride was recovered under the reduced pressure to give a pale yellow oily substance for the further usage. 2,6-Dichlorophenol (57.1 g, 0.35 mol), sodium carbonate (48.4 g, 0.35 mol) and toluene (200 mL) were placed in a flask, and the above pale yellow oil was dropwise added slowly into an ice bath. Then the reaction mixture was heated to reflux for 3 hours. The reaction solution was filtered to remove the insoluble substances. The filtrate was washed with water, concentrated and dried under vacuum to afford an orange solid as the intermediate 5 (140.62 g, 97% yield), m.p., 134~136° C. $^1$H NMR spectrum was analyzed as same as the above.

Preparation of methyl 2-(2-(N-(2,6-dichlorophenyl) benzoylamino)phenyl)ester (6)

Example 1

The intermediate 5 (124.3 g, 0.3 mol) and diphenyl ether (200 mL) were placed in a flask, which was heated to reflux for 3 hours. The reaction mixture was then cooled, from which diphenyl ether was recovered under the reduced pressure to obtain a brown solid as the intermediate 6 (124 g, 99% yield), m.p., 156~158° C. $^1$H NMR (400 MHz, CDCl$_3$) δ: 7.64 (d, J=7.6 Hz, 2H), 7.57-7.50 (m, 2H), 7.39-7.32 (m, 3H), 7.29-7.21 (m, 4H), 7.16-7.12 (m, 1H), 3.85 (s, 2H), 3.75 (s, 3H).

Example 2

The intermediate 5 (124.3 g, 0.3 mol) was placed in a flask, which was heated to melt under stirring. The melted product was further heated to 300° C. to react for 0.5 hour. The reaction was then cooled to give a brown solid as the intermediate 6 (124 g, 99% yield), m.p., 156~157° C. $^1$H NMR spectrum was analyzed as same as the above.

Preparation of Diclofenac Sodium (1)

Example 1

Sodium hydroxide (25 g, 0.625 mol) and water (58 mL) were placed in a flask, to which were added with the intermediate 6 (103.6 g, 150 mL, 0.25 mol) and methanol (150 mL) under stirring. The reaction was heated to reflux for 6 hours under stirring to the reaction was completed. The reaction solution was then allowed to cool down to room temperature, from which methanol was recovered under the reduced pressure. Water (150 mL) was added to the resulting product, which was then decolorized with activated the carbon before being filtrated and crystallized by cooling down to room temperature to afford an off-white solid as the target compound 1 (68.4 g, 86% yield), m.p., 287~289° C.

Example 2

Sodium hydroxide (25 g, 0.625 mol) and water (58 mL) were placed in a flask, to which were added with intermediate 6 (103.6 g, 150 mL, 0.25 mol) and toluene (150 mL) under stirring. The reaction was heated to reflux for 8 hours under stirring. Then the reaction solution was cooled to room temperature, from which toluene was recovered under the reduced pressure. Water (150 mL) was added to the resulting product, which was then decolorized with the activated carbon before being filtrated and crystallized by cooling to provide an off-white solid as the target compound 1 (59.6 g, 75% yield), m.p., 288~290° C.

The examples described above are merely illustrative of the present invention, which is not limited to these examples.

What is claimed is:

1. A method of synthesizing diclofenac sodium, comprising:
    step (1) ortho-nitrating phenylacetate in a solution of dichloromethane containing a nitration agent to obtain o-nitrophenylacetate;
    step (2) hydrogenating o-nitrophenylacetate in the presence of a palladium catalyst to obtain o-aminophenylacetate;
    step (3) amidating the amino group of o-aminophenylacetate to obtain 2-(2-benzoylaminophenyl) acetate;
    step (4) 2-(2-benzoylaminophenyl) acetate reacting with thionyl chloride to obtain a chloroimine intermediate, and then condensing the chloroimine intermediate with 2,6-dichlorophenol using an inorganic base to obtain (E)-methyl-2-(2-((2,6-dichloro phenoxy)(phenyl)methyleneamino)phenyl) ester;
    step (5) subjecting (E)-methyl-2-(2-((2,6-dichlorophenoxy)(phenyl) methylene amino) phenyl) ester to Chapman rearrangement to obtain methyl 2-(2-(N-(2, 6-dichlorophenyl)benzoylamino)phenyl) ester; and
    step (6) hydrolyzing methyl 2-(2-(N-(2,6-dichlorophenyl) benzoylamino)phenyl) ester with an inorganic base to obtain the target product of diclofenac sodium.

2. The method of claim 1, wherein in step (1), the nitration agent is selected from the group consisting of nitric acid, fuming nitric acid, a mixture of nitric acid and sulfuric acid, or a mixture of nitric acid and acetic acid; and an organic solvent is selected from the group consisting of dichloromethane, tetrahydrofuran, dioxane, or a mixture thereof; and a reaction temperature is −10~25° C.

3. The method of claim 1, wherein in step (1), the nitration agent is fuming nitric acid or a mixture of nitric acid and sulfuric acid; and an organic solvent is absent or dichloromethane; and a reaction temperature is from 0° C.~25° C.

4. The method of claim 1, wherein in step (2), the palladium catalyst is selected from the group consisting of Pd/C, D61-Pd, D72-Pd, D152-Pd, D261-Pd and D296-Pd; a hydrogenation pressure is from atmospheric pressure to 1.0 Mpa; an organic solvent is an alcohol of low molecular weight or an ester of low molecular weight; an organic solvent is a single solvent, or a mixed solvent; and a reaction temperature is 0~50° C.

5. The method of claim 4, wherein the palladium catalyst is Pd/C; the hydrogenation pressure is atmospheric pressure; the organic solvent is selected from the group consisting of methanol, ethanol and ethyl acetate; and the reaction temperature is 5~25° C.

6. The method of claim 1, wherein in step (3), an amidating agent is benzoyl chloride; an acid acceptor is selected from the group consisting of triethylamine, potassium carbonate and sodium carbonate; and a reaction temperature is 0~30° C.

7. The method of claim 1, wherein in step (4), the inorganic base is selected from the group consisting of sodium carbonate, potassium carbonate, sodium bicarbonate and sodium hydride; an organic solvent is selected from the group consisting of dichloromethane, dichloroethane, tetrahydrofuran, toluene and xylene; and a reaction temperature is 60~130° C.

8. The method of claim 7, wherein the inorganic base is selected from the group consisting of sodium carbonate and potassium carbonate; and the organic solvent is toluene.

9. The method of claim 1, wherein in step (5), an organic solvent is absent or selected from the group consisting of toluene, xylene and diphenyl ether; and a reaction temperature is 110~300° C.

10. The method of claim 1, wherein in step (6), the inorganic base is sodium hydroxide; an organic solvent is selected from the group consisting of toluene and methanol; and a reaction temperature is 50~150° C.

* * * * *